(12) United States Patent
Verplancke et al.

(10) Patent No.: US 12,127,957 B2
(45) Date of Patent: Oct. 29, 2024

(54) METHOD FOR INTEGRATING AN ELECTRONIC CIRCUIT IN OR ON A STENT

(71) Applicants: Universiteit Gent, Ghent (BE); IMEC VZW, Leuven (BE)

(72) Inventors: Rik Verplancke, De Pinte (BE); Jan Vanfleteren, Gentbrugge (BE)

(73) Assignees: Universiteit Gent, Ghent (BE); IMEC VZW, Leuven (BE)

( * ) Notice: Subject to any disclaimer, the term of this patent is extended or adjusted under 35 U.S.C. 154(b) by 727 days.

(21) Appl. No.: 17/298,674

(22) PCT Filed: Nov. 28, 2019

(86) PCT No.: PCT/EP2019/082839
§ 371 (c)(1),
(2) Date: Jun. 1, 2021

(87) PCT Pub. No.: WO2020/114871
PCT Pub. Date: Jun. 11, 2020

(65) Prior Publication Data
US 2022/0015930 A1    Jan. 20, 2022

(30) Foreign Application Priority Data

Dec. 6, 2018  (EP) ..................... 18210723

(51) Int. Cl.
*A61F 2/86*    (2013.01)
*A61N 5/06*    (2006.01)

(52) U.S. Cl.
CPC .............. *A61F 2/86* (2013.01); *A61N 5/0601* (2013.01); *A61N 5/0622* (2013.01);
(Continued)

(58) Field of Classification Search
CPC ...... A61F 2/82; A61F 2/86; A61F 2/91; A61F 2/92; A61B 5/6862
See application file for complete search history.

(56) References Cited

U.S. PATENT DOCUMENTS

| | | | |
|---|---|---|---|
| 11,284,840 B1* | 3/2022 | Xu ..................... | A61B 5/02152 |
| 2004/0254630 A1* | 12/2004 | Yang ........................ | A61F 2/91 |
| | | | 623/1.15 |

(Continued)

FOREIGN PATENT DOCUMENTS

| | | |
|---|---|---|
| WO | 01/32104 A1 | 5/2001 |
| WO | 02/058549 A1 | 8/2002 |

(Continued)

OTHER PUBLICATIONS

Kirsten, Sabine et al: "Biocompatible packaging for implantable miniaturized pressure sensor device used for stent grafts: Concept and choice of materials", 2014 IEEE 16th Electronics Packaging Technology Conference (EPTC), IEEE, Dec. 3, 2014 (Dec. 3, 2014), pp. 719-724, XP032730974, DOI: 10.1109/EPTC.2014.7028327.

(Continued)

*Primary Examiner* — Diane D Yabut
(74) *Attorney, Agent, or Firm* — N.V. Nederlandsch Octrooibureau

(57) ABSTRACT

The present invention relates to a method for integrating an electronic circuit in or on a medical stent. The method comprises obtaining (101) a deformable medical stent (21) in a substantially planar shape, in which the deformable medical stent is adapted for being deployed in a substantially cylindrical shape in the body. The method also comprises attaching (104) a deformable electronic circuit (22) onto the deformable medical stent in the planar shape thereby forming a deformable hybrid structure. The method also comprises shaping (107) said hybrid structure into the cylindrical shape.

13 Claims, 4 Drawing Sheets

(52) U.S. Cl.
CPC ............... *A61F 2210/0014* (2013.01); *A61F 2210/0057* (2013.01); *A61F 2220/005* (2013.01); *A61F 2250/006* (2013.01); *A61N 2005/0602* (2013.01); *A61N 2005/0632* (2013.01); *A61N 2005/0652* (2013.01)

(56) References Cited

U.S. PATENT DOCUMENTS

| | | |
|---|---|---|
| 2005/0080346 A1 | 4/2005 | Gianchandani |
| 2005/0085895 A1* | 4/2005 | Brown ................ G01R 33/286 623/1.15 |
| 2014/0107768 A1 | 4/2014 | Venkatasubramanian |

FOREIGN PATENT DOCUMENTS

| | | |
|---|---|---|
| WO | 2017/070252 A1 | 4/2017 |
| WO | 2017/075138 A1 | 5/2017 |

OTHER PUBLICATIONS

Avantor NuSil Inc.: "Biomaterials Implant Line: MED-6215 Optically clear low consistency silicone elastomer", Jan. 1, 2018 (Jan. 1, 2018), pp. 1-3, XP055654971, Retrieved from the Internet: URL: https://nusil.com/services/downloadfile.ashx?productcode=MED-6215&originalname=MED-6215.pdf [retrieved on Jan. 6, 2020].

* cited by examiner

METHOD FOR INTEGRATING AN ELECTRONIC CIRCUIT IN OR ON A STENT

FIELD OF THE INVENTION

The invention relates to the field of medical devices, e.g. to the field of intravascular implantable devices. More specifically it relates to a stent comprising an electronic circuit and a method for manufacturing such stent.

BACKGROUND OF THE INVENTION

Expandable stents are used for various medical applications, as known in the art. For example, in common medical procedures, a stent may be used to improve flow through an occluded blood vessel. Furthermore, stents may comprise electrical devices, e.g. electrodes, for sensing and/or stimulating biological systems, e.g. neurons and/or muscles, as known in the art. In the field of optogenetics, it has also been demonstrated that genetically modified neurons can be stimulated by light. For example, light stimulation may be provided by an external laser through the skull. However, this approach can be disadvantageously invasive. Therefore, transvascular light stimulation might be preferable, e.g. by a device placed inside a vein. For example, a light source in the sinus sagittalis superior could be used to provide stimulation to the motor cortex. It is an advantage of optogenetic stimulation that a good temporal and spatial control over neuron activity can be achieved. For example, by intervention in the neural activity in the motor cortex, suppression of epilepsy seizures may be achieved. Furthermore, research applications of optogenetics may enable or facilitate the mapping and identification of networks in the brain.

Therefore, a need exists in the art for efficient means to deliver electrical and/or optical stimulation to neurons in the body and/or to acquire sensor signals from within the body.

Stents, as known in the art, may be deployed in a blood vessel by using various instruments, such as introducer sheaths, catheters, guide wires and/or angioplasty expansion balloons. Self-expanding stents, e.g. which have elastic or super-elastic properties, may be used to avoid the use of, or at least reduce the pressure requirements of, an expansion balloon. Shape memory alloys (SMA), such as nitinol-based alloys, advantageously can have super-elastic properties when exposed to a temperature near the body temperature, and advantageously can be shaped in a thin strut pattern to form a compact and easily manipulatable stent, as known in the art.

The international patent application WO 2017/070252 discloses devices, methods and systems for transmitting signals via an intravascular device for stimulating and/or sensing activity of media proximal to the device, e.g. of a body tissue or fluid. In the disclosed approach, electrical components, such as platinum disc electrodes for electrical recording, are attached, individually, on a medical stent, e.g. onto cross-links, nodes or struts of the stent. Each electrode is then connected to a separate conductive wire. The wires are wrapped around the stent and along a shaft to form a wire bundle or cable, protected by an insulating sheath, to interface with the external world. However, it may be a disadvantage of such approach that the processing and/or control of the electrodes is performed externally, e.g. by an external controller connected via the wire bundle to the device.

For electrical or optogenetic stimulation of the neurons, it would be advantageous to provide compact and/or autonomous active electronic devices integrated in or fixed onto a medical stent. By locally providing resources for processing sensor signals and/or control signals for stimulating means, e.g. electrodes or light sources, a better integration can be achieved and the need for connecting wires to external components can be reduced or even avoided. Furthermore, an autonomous device, such as an optogenetic stimulator, may allow or facilitate a continuous monitoring, e.g. similar to the level of autonomy of pacemaker devices, e.g. to provide detection and suppression of epileptic seizures.

SUMMARY OF THE INVENTION

It is an object of embodiments of the present invention to provide methods for integrating an electronic circuit in or on a medical stent, e.g. an intravascular stent, such as a deformable or self-expanding intravascular stent.

The above objective is accomplished by a method according to the present invention.

It is an advantage of embodiments of the present invention that a compact and/or autonomous active electronic device can be integrated in or fixed onto a medical stent, such as a deformable intravascular stent.

It is an advantage of embodiments of the present invention that the electronic circuit may be deformed together with the medical stent.

It is an advantage of embodiments of the present invention that the electronic circuit may be reversibly deformed together with the medical stent.

It is an advantage of embodiments of the present invention that the electrical functionality of the electronic circuit can be chosen independently from the mechanical functionality of the medical stent.

It is an advantage of embodiments of the present invention that the integration of the electronic circuit on the medical stent has a minor impact on the deformability of the stent.

It is an advantage of embodiments of the present invention that an electronic circuit with a random electronic functionality can be integrated on a medical stent.

It is an advantage of embodiments of the present invention that the cylindrical hybrid structure is able to deform simultaneously in both longitudinal and radial direction, which may for instance be advantageously used for insertion of the hybrid structure in a guiding catheter to allow a simultaneous reduction of the diameter of the cylindrical hybrid structure and an increase of the length of the cylindrical hybrid structure.

It is an advantage of embodiments of the present invention that sensors and/or stimulator elements, e.g. electrodes and/or light sources, can be easily and efficiently integrated in a stent.

It is an advantage of embodiments of the present invention that resources can be provided locally in or on a stent for processing sensor signals and/or control signals for stimulating means, e.g. electrodes and/or light sources.

It is an advantage of embodiments of the present invention that a good integration of an electronic circuit can be achieved in or on a stent.

It is an advantage of embodiments of the present invention that the need for connecting wires from an active stent to external components can be reduced or avoided.

It is an advantage of embodiments of the present invention that an electronic circuit for amplifying, filtering, digitally converting, multiplexing, wired/wirelessly transmitting/receiving of signals can be provided in or on a medical stent.

It is an advantage of embodiments of the present invention that a sensing circuit and/or light source, e.g. light emitting diodes, for optogenetic stimulation can be integrated in or on a medical stent.

It is an advantage of embodiments of the present invention that an autonomous active implant can be deployed in the body, e.g. in a blood vessel.

In a first aspect, the present invention relates to a method for integrating an electronic circuit in or on a medical stent. The method comprises obtaining a deformable medical stent in a substantially planar shape, wherein said deformable medical stent is adapted for being deployed in a substantially cylindrical shape in the human or animal body. The method comprises attaching a deformable electronic circuit onto the deformable medical stent when in said substantially planar shape, thereby forming a deformable hybrid structure. The method comprises shaping said deformable hybrid structure, i.e. said deformable medical stent together with the deformable electronic circuit attached thereon, into said substantially cylindrical shape.

In a method in accordance with an embodiment of the present invention, obtaining a deformable medical stent in a substantially planar shape may comprise obtaining a deformable medical stent in a substantially cylindrical shape and deforming said substantially cylindrical shape into said substantially planar shape.

In a method in accordance with an embodiment of the present invention, the deformable electronic circuit may be a stretchable electronic circuit.

In a method in accordance with embodiments of the present invention, said deformable hybrid structure is a reversibly deformable hybrid structure.

In a method in accordance with embodiments of the present invention, attaching of said deformable electronic circuit may comprise obtaining said deformable electronic circuit comprising at least one active electronic component.

In a method in accordance with embodiments of the present invention, said deformable electronic circuit may comprise at least one light emitting diode and/or at least one sensor element, and deformable electrical connections connected to said at least one light emitting diode and/or said at least one sensor element.

In a method in accordance with embodiments of the present invention, obtaining of said deformable medical stent may comprise obtaining said deformable medical stent comprising at least one wire and/or a plurality of struts, configured to form a three-dimensional mesh structure, wherein said three-dimensional mesh structure forms said substantially cylindrical shape and wherein said substantially cylindrical shape is interrupted by a longitudinal cut such that said mesh structure can be flattened into said substantially planar shape.

A method in accordance with embodiments of the present invention may comprise providing regions of decreased thickness and/or holes in said deformable electronic circuit, and attaching of said deformable electronic circuit may comprise aligning said regions or holes to openings in said mesh structure of said deformable medical stent. Providing said regions and/or holes in said deformable electronic circuit may be performed after said attaching.

In a method in accordance with embodiments of the present invention, obtaining of said deformable medical stent may comprise obtaining said deformable medical stent comprising or consisting of an elastic material or a super-elastic material.

In a method in accordance with embodiments of the present invention, obtaining of said deformable medical stent may comprise obtaining said deformable medical stent comprising or consisting of a shape-memory alloy, SMA, having a stable geometrical configuration in its austenite phase that corresponds to said substantially cylindrical shape.

In a method in accordance with embodiments of the present invention, obtaining said deformable medical stent may comprise deforming said deformable medical stent into said substantially planar shape at an ambient temperature below room temperature to bring said SMA material in its martensitic phase.

A method in accordance with embodiments of the present invention may comprise temporarily fixating said deformable medical stent in said substantially planar shape.

In a method in accordance with embodiments of the present invention, attaching of said deformable electronic circuit may comprise attaching said deformable electronic circuit onto said deformable medical stent on a side thereof that is directed radially inward in the substantially cylindrical shape and/or attaching said deformable electronic circuit, or a further deformable electronic circuit, on a side thereof that is directed radially outward in the substantially cylindrical shape.

In a method in accordance with embodiments of the present invention, attaching of said deformable electronic circuit to said deformed medical stent may comprise encapsulating the deformable electronic circuit and the deformed medical stent in between two encapsulation layers that are fused and/or glued together.

A method in accordance with embodiments of the present invention may comprise manufacturing the deformable electronic circuit before the step of attaching.

In a second aspect, the present invention relates to a deformable medical stent comprising a deformable medical stent structure for being deployed in a substantially cylindrical shape in a human or animal body and a deformable electronic circuit attached onto the deformable medical stent structure.

In a deformable medical stent in accordance with embodiments of the present invention, the deformable medical stent structure may comprise a three-dimensional mesh structure and may comprise an elastic material or a super-elastic material.

In a deformable medical stent in accordance with embodiments of the present invention, the deformable electronic circuit may comprise at least one active electronic component.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
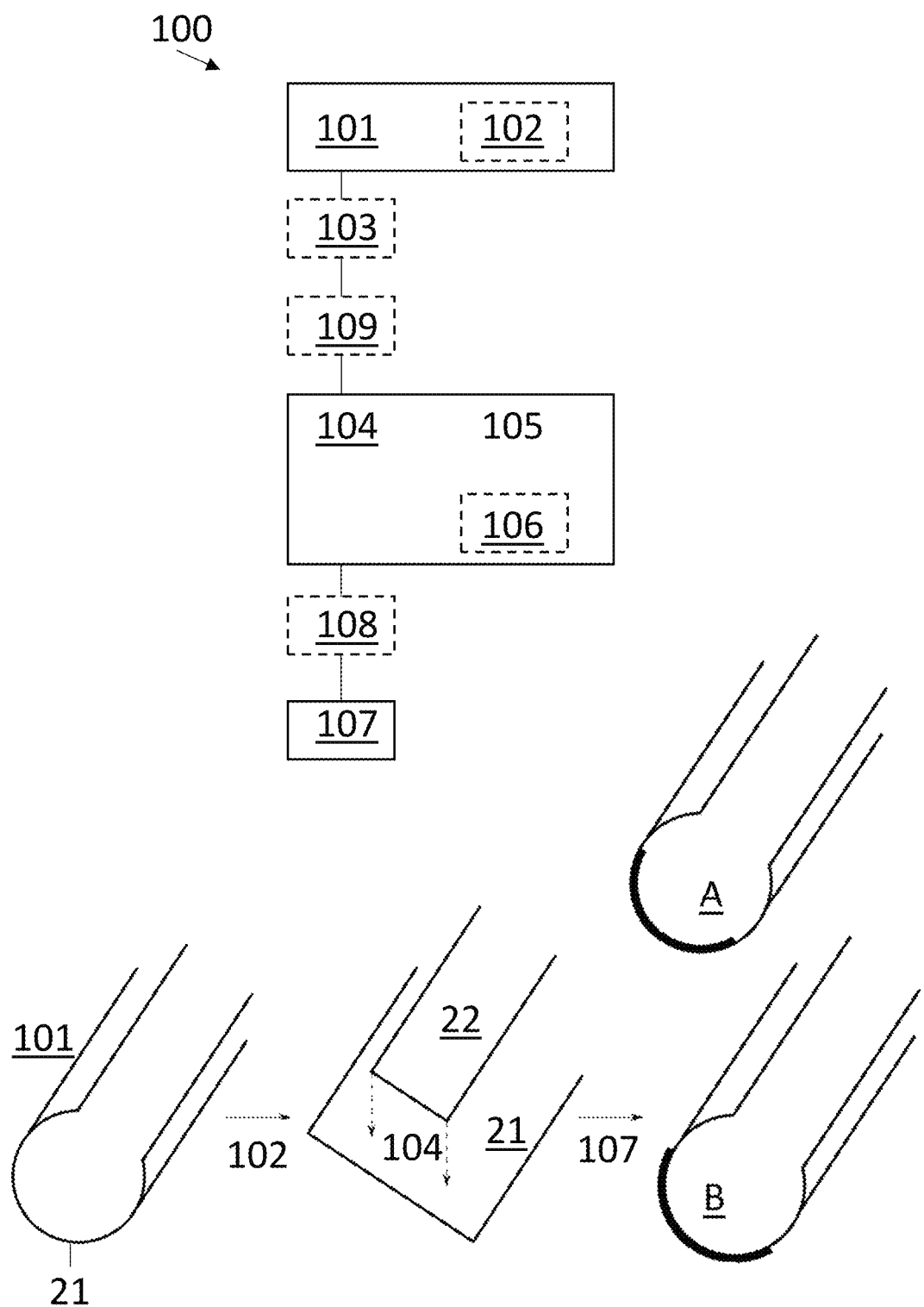
FIG. 1 shows an exemplary method and an exemplary deformable medical stent in accordance with embodiments of the present invention

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a method for integrating an electronic circuit in or on a medical stent. The method comprises obtaining a deformable medical stent, such as a self-expanding intravascular stent, in a substantially planar shape, in which the deformable medical stent is adapted for being deployed in a substantially cylindrical shape in the human or animal body, e.g. in a blood vessel. The method comprises attaching a deformable electronic circuit, e.g. a flexible and/or stretchable and/or extensible and/or compressible electronic circuit, on the deformable medical stent in the substantially planar shape. The method comprises shaping the deformable medical stent having the deformable electronic circuit attached thereon into a cylindrical shape.

Referring to FIG. 1, an exemplary method 100 in accordance with embodiments of the present invention is shown. The method 100 provides an integration of an electronic circuit, e.g. an active electronic circuit, e.g. an integrated circuit comprising at least one active electronic component, in or on a medical stent. The active electronic component may, for example, comprise a light emitting diode.

The method 100 comprises obtaining 101 a deformable medical stent in a substantially planar shape. The deformable medical stent is adapted for being deployed in a substantially cylindrical shape in the body, e.g. in a blood vessel, in or near the heart, such as in or near a heart valve, in the gastrointestinal system, such as in the colon or intestines, in the lungs and/or in the ureter or urethra. For example, FIG. 2 schematically shows a deformable medical stent 21, in the shape of a three-dimensional mesh.

Figure 2:
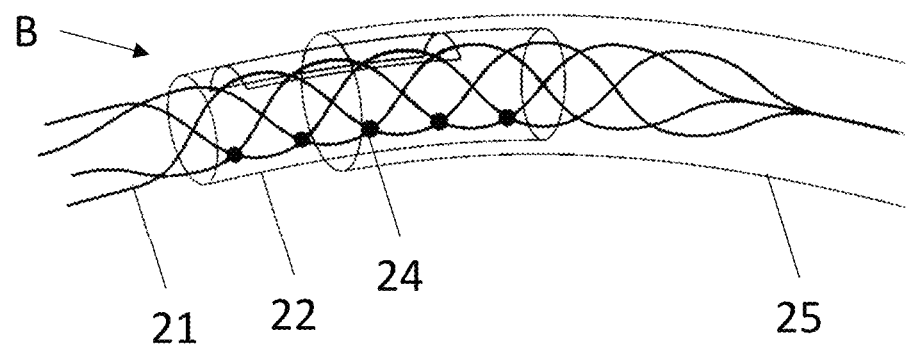
FIG. 2 shows a deformable medical stent in accordance with embodiments of the present invention.
Figure 3:
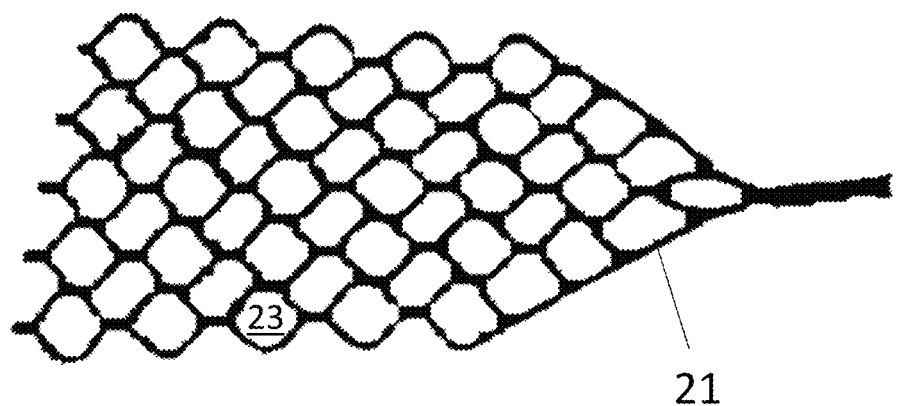
FIG. 3 illustrates a deformable medical stent structure, deformed into a planar shape, in accordance with embodiments of the present invention.

For example, FIG. 2 illustrates a deformable medical stent being deployed in its substantially cylindrical shape, while FIG. 3 illustrates a similar deformable medical stent in its substantially planar shape.

Where reference is made to a 'medical stent,' this should not be interpreted as a stent that is exclusively used or usable for medical applications, but also similar stents for related purposes, such as biological research or veterinary applications. The deformable medical stent may be a deformable intravascular stent, e.g. a deformable stent that can be deployed inside a blood vessel, or a deformable stent for deployment in another body vessel or cavity.

The deformable medical stent may comprise a self-expanding intravascular stent. The deformable medical stent may be reversibly deformable between a substantially cylindrical shape to a substantially planar shape, e.g. by bending and/or rolling the stent in its substantially planar shape around an axis to obtain a substantially cylindrically symmetric shape, e.g. forming a cylinder interrupted by a longitudinal cut such that the structure can be flattened into the substantially planar shape.

For example, the substantially planar shape of the deformable medical stent may refer to a shape that is a topologically open surface, e.g. that is homeomorph to a plane, and does not deviate substantially from the planar shape, e.g. deviating less than 20%, e.g. less than 10%, e.g. less than 5%, when evaluating the ISO-12781 peak-to-valley flatness over the maximum in-plane diameter.

In embodiments in accordance with the present invention, the deformable medical stent may comprise, e.g. may be composed of, an elastic material or a super-elastic material.

In embodiments in accordance with the present invention, the deformable medical stent may comprise, e.g. may be composed of, a shape-memory alloy (SMA).

For example, the medical stent comprising the shape-memory alloy may have a stable geometrical configuration in its austenite phase. This stable geometrical configuration may correspond to the substantially cylindrical shape. SMA materials advantageously can have super-elastic properties, e.g. can reversibly deform, even under a large strain, from the 'programmed' shape. For example, the SMA material may comprise a Nickel-Titanium alloy, e.g. nitinol, or alloys comprising Nickel and Titanium, such a Nickel-Titanium-Hafnium or Nickel-Titanium-Palladium alloy. For example, the SMA material may comprise a Nickel-Titanium alloy having about 45% to 60 wt % of Nickel, e.g. a ratio of Ni/Ti in the range of 50:50 to 51.5:48.5. Other exemplary SMA materials include Silver-Cadmium, Gold-Cadmium, Copper-Aluminium-Nickel, Copper-Tin, Copper-Zinc, Iron-Platinum, Manganese-Copper, Iron-Manganese-Silicon, Copper-Nickel-Aluminium, Copper-Nickel-Gallium, Nickel-Iron-Gallium, Titanium-Niobium, and Nickel-Manganese-Gallium. SMA materials may require a high temperature for setting the parent shape, e.g. of about 500° C. for nitinol. This complicates the integration of active electronic circuitry on the stent, since such high temperature step cannot be performed on the stent on which the active electronics are integrated, e.g. because the high temperature could damage the electronics. Therefore, it is an advantage of embodiments of the present invention that a good and efficient integration of active electronic circuits on SMA stents can be obtained. The SMA material may be provided with a coating to provide or improve biocompatibility, such as a passive titanium oxide layer, e.g. $TiO_2$.

However, in a method in accordance with embodiments of the present invention, the SMA material may also be a low-temperature programmable material, e.g. programmable at a temperature below 300° C. For example, the method may also comprise programming the parent shape after shaping the deformable medical stent having the deformable electronic circuit attached thereon into the cylindrical shape.

The deformable medical stent, e.g. a medical stent comprising or consisting of a SMA material, may comprise one or more wires (e.g. of the SMA material) that are shaped, e.g. intertwined, to form a three-dimensional mesh structure. Alternatively, such mesh structure may also be manufactured by perforating a hollow cylinder, e.g. by laser cutting. The mesh structure may form the substantially cylindrical shape, e.g. in which the substantially cylindrical shape is interrupted by a longitudinal cut such that the mesh structure can be flattened into the substantially planar shape. For example, the mesh structure may comprise a wire (or wires) having a diameter in the order of 20 μm to 150 μm, e.g. in the range of 50 μm to 75 μm.

However, embodiments of the present invention are not necessarily limited thereto. For example, the deformable medical stent may comprise any suitable material and have any shape such that it can be deployed in a predominantly cylindrical shape in the body. For example, the deformable medical stent may comprise a deformable predominantly cylindrical body, and the deformable medical stent may have a longitudinal cut such that the cylindrical body can be unfolded and flattened into a substantially planar shape. For example, the step of obtaining 101 may comprise cutting the medical stent in the substantially cylindrical shape, e.g. along its axial direction, such that the medical stent can be unfolded and flattened.

Obtaining 101 the deformable medical stent may comprise deforming 102 the medical stent into the substantially planar shape, e.g. unfolding the medical stent in the substantially cylindrical shape to obtain the substantially planar shape. Preferably, the medical stent is adapted for reversibly deforming from the substantially cylindrical shape to the substantially planar shape, e.g. by applying a suitable force. Furthermore, for embodiments in which the deformable medical stent comprises a SMA material, the step of deforming 102 the medical stent may be performed at or near room temperature. However, the step of deforming 102 the (SMA) medical stent may also be performed at an ambient temperature below room temperature, e.g. to bring the SMA material (substantially) in its martensitic phase, which advantageously allows a good plastic deformation while this deformation is (substantially) fully reversible, e.g. by retaining a shape memory of the parent shape.

The method 100 may comprise temporarily fixating 103 the medical stent in the substantially planar shape, e.g. by means of a dissolvable glue, clamps, pins or similar means for fixation. It is an advantage of a stent comprising a SMA that the shape of the stent can return to the substantially cylindrical shape, e.g. the parent shape, by releasing the temporary fixation.

Figure 4:
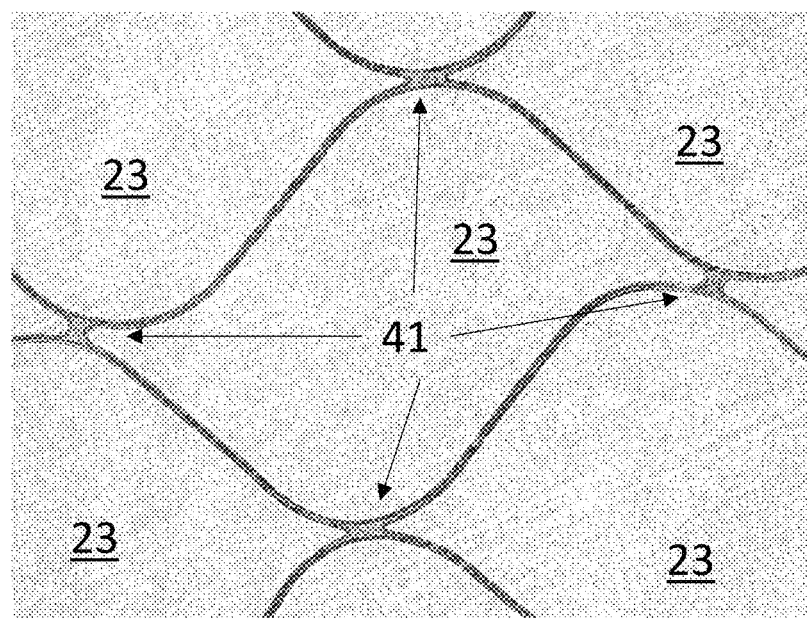
FIG. 4 illustrates a mesh structure of a deformable medical stent structure, in accordance with embodiments of the present invention.

The method comprises attaching 104 a deformable electronic circuit on the deformed medical stent. For example, FIG. 2 illustrates the deformable electronic circuit 22 attached to the deformable medical stent 21. For example, the deformable electronic circuit may comprise at least one biostimulator element, such as electrodes for electrical stimulation and/or light sources for optical stimulation, e.g. light emitting diodes (LEDs). Thus, a LED may be integrally formed on or in the deformable electronic circuit, or attached to the deformable electronic circuit, e.g. soldered, glued by conductive glue or attached by another suitable technique for operably connecting electronic components to a deformable integrated circuit. However, the LED or LEDs may also be attached to the medical stent separately and connected to the deformable electronic circuit, e.g. by a wire(s). For example, referring to FIG. 2 and FIG. 4, a LED 24 may be attached at a node 41 (e.g. a joint) of a mesh structure of the medical stent, e.g. by gluing, suturing or by another attachment technique known in the art, and connected to the deformable electronic circuit. For example, connecting wires may be wrapped around wires or struts of the mesh structure of the medical stent, or interconnecting metal lines may be integrated in the deformable electronic circuit.

For example, embodiments not limited thereto, the biostimulator element may comprise a blue light emitting LED having an output power in the range of 1 mW to 100 mW, e.g. in the range of 5 mW to 25 mW, e.g. 10 mW. For example, the deformable electronic circuit may comprise a pulse frequency generator for generating a predetermined frequency of stimulation pulses for the biostimulator element, e.g. to generate an optical stimulation in the range of 1 Hz to 200 Hz, e.g. in the range of 5 Hz to 50 Hz, e.g. 10 Hz. For example, the pulse frequency generator may operate on a duty cycle in the range of 0.1 to 10%, e.g. in the range of 0.5 to 5%, e.g. of about 1%. For example, a 1 ms pulse of light may be generated in each interval of 100 ms, e.g. corresponding to a frequency of 10 Hz and a duty cycle of 1%.

In embodiments of the present invention the deformability of the electronic circuit is adapted to the deformability of the deformable stent such that, upon shaping the deformable medical stent together with the deformable electronic circuit attached thereon from a planar shape to a substantially cylindrical shape, the electronic circuit is able to follow the deformation of the medical stent thereby preventing or decreasing a risk for delamination of the electronic circuit from the stent structure.

In embodiments of the present invention the deformability of the electronic circuit is adapted to the deformability of the deformable stent such that the electronic circuit is able to follow the deformation of the medical stent in use, e.g. upon insertion of the cylindrical hybrid structure in an insertion catheter, thereby preventing or decreasing a risk for delamination of the electronic circuit from the stent structure.

In embodiments of the present invention, the hybrid structure deforms elastically upon shaping the hybrid structure from its planar shape into the substantially cylindrical shape.

In embodiments of the present invention, the hybrid structure deforms elastically in use, allowing the cylindrical hybrid structure to deform simultaneously in radial and longitudinal direction, e.g. to change from a first cylindrical form factor (having a first diameter and first length) to a second cylindrical form factor (having a second diameter and second length, the second diameter being smaller than the first diameter and the second length being larger than the first length or vice versa).

In embodiments of the present invention, the deformability of the hybrid structure is adapted such that the elastic limit of the hybrid structure, i.e. the load beyond which the hybrid structure no longer behaves elastically, is determined taking into account the maximal deformation of the medical stent in use. As an example, without being limited thereto, for an intravascular medical stent, the maximal deformation may be calculated using the difference between the diameter of the lumen and the diameter of the catheter through which the stent is inserted into the lumen. Such electronic circuit is less prone to damage when shaping said hybrid structure into said cylindrical shape.

In embodiments of the present invention, the deformable electronic circuit is a stretchable electronic circuit. A hybrid cylindrical structure comprising such a stretchable electronic circuit has the advantage that the distance between two random points on the cylindrical surface of the hybrid cylindrical structure may be changed, i.e. increased or decreased, reducing the risk for delamination of the electronic circuit from the stent structure upon deformation (in use as well as when deforming from a planar state to a cylindrical state). Preferably, both the electronic circuit as well as the medical stent are stretchable.

In embodiments of the present invention, the deformable electronic circuit is able to follow the deformation of the medical stent in both longitudinal direction (i.e. a direction parallel to the axis of the medical stent) and radial direction (i.e. a direction perpendicular to the axis of the medical stent). Preferably, the deformable electronic circuit is able to follow the deformation of the medical stent in a simultaneous longitudinal and radial direction.

The deformable electronic circuit may be attached to the deformed medical stent on a side thereof that is directed radially inward in the substantially cylindrical shape of the medical stent, e.g. on a side of the stent that was convex before the step of deforming 102 the medical stent into the substantially planar shape. For example, an exemplary medical stent A having the circuit attached thereto on this side, after (re)shaping to its substantially cylindrical shape, is shown in FIG. 1. It is an advantage that, when reshaped to its substantially cylindrical shape, elastic resilience of the deformable structure, e.g. a tendency to return to its planar shape, can push the deformable electronic circuit against the medical stent, thus preventing or decreasing a risk for delamination and/or assisting in the deformation of the medical stent to its substantially cylindrical shape.

Alternatively or additionally, the deformable electronic circuit may be attached to the deformed medical stent on a side thereof that is directed radially outward in the substantially cylindrical shape of the medical stent. For example, an exemplary medical stent B having the circuit attached thereto on this side, after (re)shaping to its substantially cylindrical shape, is shown in FIG. 1. For example, attaching 104 a deformable electronic circuit on the deformed medical stent may comprise attaching a first deformable electronic circuit on a first side of the deformed medical stent and attaching a second deformable electronic circuit on a second side of the deformed medical stent. The first deformable electronic circuit and the second deformable electronic circuit may be configured to operate independently, or may be interconnected. For example the first deformable electronic circuit may provide functionality directed towards the bloodstream when the stent is deployed in the body, e.g. in a blood vessel, for example for sensing of properties of the blood stream, and the second deformable electronic circuit may provide functionality directed towards the wall of, or tissue in the vicinity of, the body structure in which the stent is deployed, e.g. of the blood vessel, such as electrical or optical stimulation, e.g. by LEDs.

The deformable electronic circuit may comprise, for example, a patterned flexible printed circuit board (PCB). For example, the deformable electronic circuit may comprise a thin-film based flexible electronic circuit. For example, the deformable electronic circuit may comprise a polyimide substrate. For example, a polyimide substrate and thin-film metal interconnections on the substrate may be patterned so that they are deformable, e.g. extensible and/or stretchable and/or compressible.

The deformable electronic circuit may comprise regions of decreased thickness or (through)holes 61. For example, the deformable electronic circuit, e.g. a flexible electronic circuit, may be perforated (e.g. etched away) in regions where no electronic circuit elements are provided in or on the deformable electronic circuit. These regions of decreased thickness or (through)holes 61 may be provided in the deformable electronic circuit before the attachment 104, or may, advantageously, be created after the attachment 104.

Figure 6:
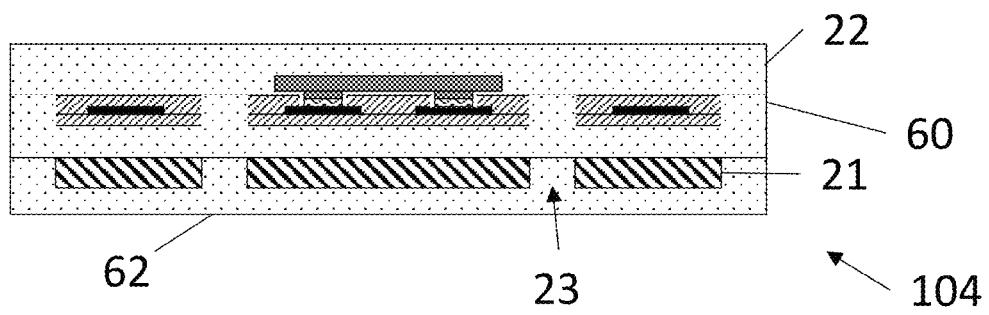
FIG. 6 shows a deformable medical stent structure and a flexible electronic circuit encapsulated together by an encapsulation material, in accordance with embodiments of the present invention.

These regions of decreased thickness or holes 61 may correspond to openings 23 in the medical stent, e.g. may be aligned when attached 104 to such openings, e.g. as illustrated in FIG. 6. For example, the medical stent may comprise a mesh structure, and the regions of reduced thickness or holes of the deformable electronic circuit may correspond to openings 23 in this mesh structure, e.g. to openings between a meshed wire (or wires) forming the medical stent. Thus, the pattern of the regions or holes 61 in the deformable electronic circuit may overlap with the openings 23 in a mesh of the stent (even though the size of each region or hole is not necessarily identical to that of the corresponding opening in the stent). Electronic components on the deformable electronic circuit may thus be positioned, after attachment 104, at the position of crosslinks and/or nodes and/or struts of the mesh forming the stent. For example, electrical conductors, e.g. signal and/or power supply lines for interconnecting electronic components of the circuit, may be aligned along the wires or struts of the mesh after attachment 104. For example, the deformable electronic circuit may be characterized by straight interconnection lines that may correspond to (at least part of) the mesh structure of the stent in its substantially planar shape.

However, in other embodiments in accordance with embodiments of the present invention, the regions or holes in the deformable electronic circuit may not necessarily overlap or fully overlap with the openings in the medical stent. Thus, an electronic circuit can be provided that is more complex than room provided by the structural elements of the stent, e.g. of wires, struts, cross-links and/or nodes of a mesh forming the stent, would allow for. For example, the deformable electronic circuit may comprise meandering electrical conductors, e.g. signal and/or power supply lines, such that these electrical conductors can be less prone to damage due to stretching, e.g. elongation in at least one direction, of the deformable circuit.

Figure 5:
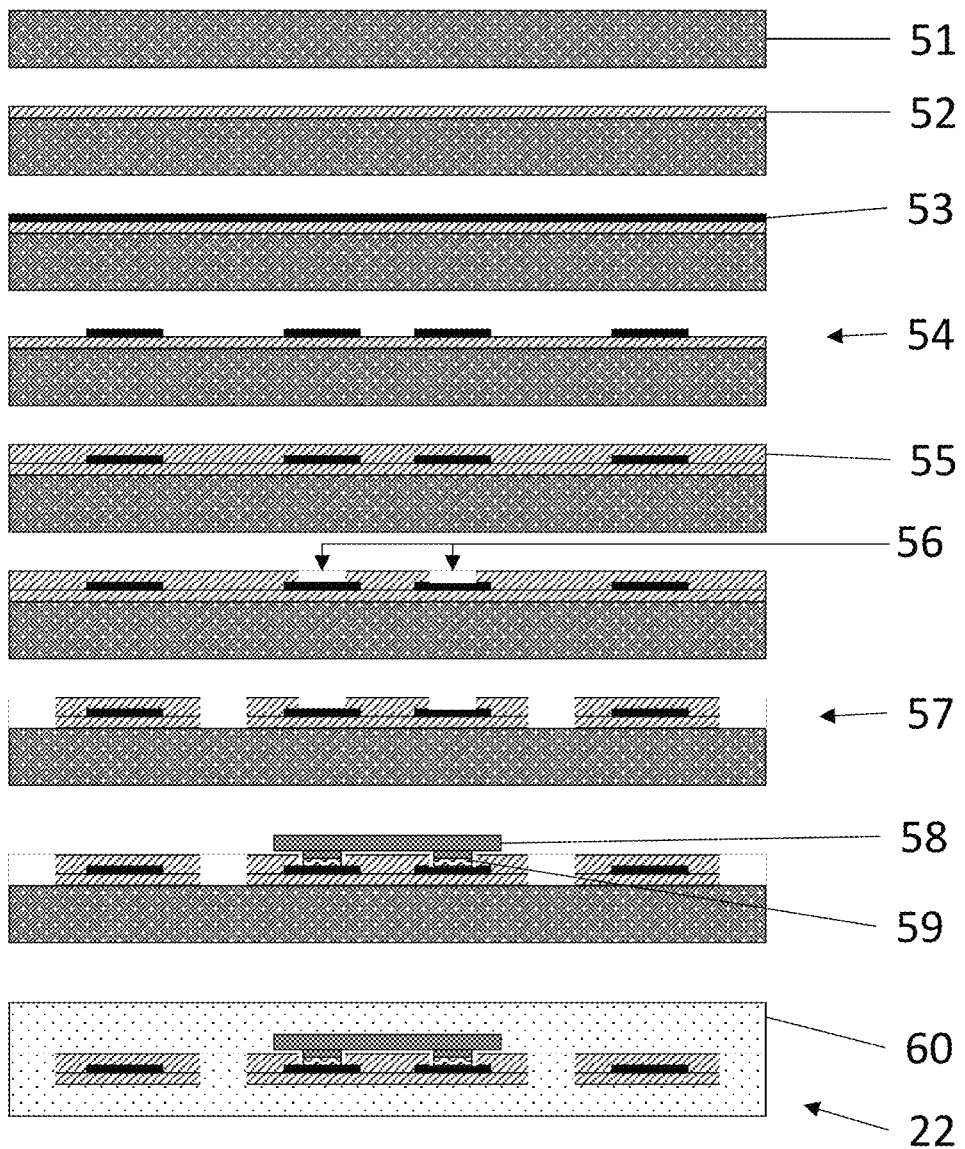
FIG. 5 illustrates a process of manufacturing a flexible electronic circuit in a method in accordance with embodiments of the present invention, and an exemplary flexible electronic structure for use in a deformable medical stent in accordance with embodiments of the present invention.

Referring to FIG. 5, the deformable electronic circuit may comprise an electrically insulating material 60, e.g. at least two insulating layers, e.g. a bottom layer and a top layer, for electrically isolating the deformable electronic circuit from the medical stent (when attached thereto). For example, the electronic circuit, e.g. electronic components and/or electrical conductors thereof, may be embedded in the electrically insulating material, e.g. between two insulating layers. The insulating material may comprise an electrically insulating polymer material, such as polyimide, thermoplastic polyurethane (TPU) or other polymer insulators suitable for flexible electronic circuits known in the art, or a combination of such materials, e.g. in a combination of multiple layers. Preferably, the at least two insulating layers may have bidirectional barrier layer properties, e.g. such as to protect the electronic circuit from the environment in the body, e.g. molecules in the body that could cause malfunction by corrosion of the electronic circuit, and such as to block any diffusion of non-biocompatible materials in the deformable electronic circuit into the body. Methods known in the art for making electronics biocompatible may be applied in providing the deformable electronic circuit.

Advantageously, the deformable electronic circuit may be multi-layered, e.g. to provide complex electronic functionality. It is an advantage of embodiments of the present invention that good integration of a complex electronic circuit on a medical stent can be provided. For example, the deformable electronic circuit may comprise a wireless data transmitter and/or receiver. Likewise, the deformable electronic circuit may comprise a wireless power receiver for wirelessly receiving a power supply from an external source. However, embodiments of the present invention are not necessarily limited thereto, e.g. the deformable electronic circuit may be configured to perform a predetermined function autonomously, e.g. without requiring data exchange with the outside world, or the deformable electronic circuit may comprise at least one wire lead, e.g. a conductive wire, such as an electrically insulated electrical wire, to exchange data and/or to receive power from the outside world. Nevertheless, even if the circuit is connected to the outside world via a wire lead, embodiments of the present invention may still provide signal manipulation functions integrated in the deformable electronic circuit, e.g. for amplifying, filtering, processing, digitizing and/or multiplexing signals received or transmitted via the wire lead. Therefore, the requirements of the signal lead connecting the device to the outside world may be reduced compared to prior-art solutions, e.g. fewer signal leads, less shielding against EM interference and/or a lesser diameter of the conductor(s) may be achieved.

Attaching 104 the deformable electronic circuit to the deformed medical stent may comprise establishing a durable mechanical connection, e.g. by gluing, over the entire contact surface between the stent and the circuit, but the attaching 104 may also comprise establishing such durable mechanical connection between only a plurality of (discrete) contact points between the deformable electronic circuit and the deformed medical stent.

Attaching 104 the deformable electronic circuit to the deformed medical stent may comprise gluing 105 the deformable electronic circuit to the deformed medical stent.

Attaching 104 the deformable electronic circuit to the deformed medical stent may comprise encapsulating 106 the deformable electronic circuit and the deformed medical stent between two encapsulation layers, e.g. sandwiching the deformable electronic circuit together with the medical stent between two layers which are fused and/or glued together.

Referring to FIG. 6, the step of encapsulating 106 may comprise providing the deformed (e.g. planarized) medical stent on a bottom encapsulation layer 62, providing the deformable electronic circuit on the deformed medical stent and providing a top encapsulation layer on the deformable electronic circuit. The top encapsulation layer may, for example, be provided on the deformable integrated circuit as obtained or as manufactured 109, e.g. in the form of the electrically insulating material 60.

The step of encapsulating may further comprise fusing and/or gluing the bottom encapsulation layer and the top encapsulation layer together to encapsulate the deformed medical stent and the deformable electronic circuit. However, the step of encapsulating 106 the deformable electronic circuit may also comprise alternative approaches to embed the deformable electronic circuit in the encapsulation material, e.g. by casting. For example, the encapsulation material, e.g. the bottom and top encapsulation layers, may comprise a polymer material, such as polyimide, thermoplastic polyurethane (TPU) or other suitable materials.

Thus, the deformable electronic circuit can be laminated to the medical stent, e.g. to an SMA material mesh forming a stent. For example, for a medical stent comprising perforations or openings 23, such as a stent being formed from a mesh, a lamination, e.g. between the bottom and top encapsulating layers, may be preferable, e.g. due to the narrow and limited contact area provided by the stent. Thus, by flattening the stent structure and sandwiching the stent and the circuit between two layers, a good encapsulation can be achieved. The layers may subsequently be attached together, e.g. by heating and exerting pressure. Flattening and/or unfolding of the stent may enable an accurate processing of the step of attaching and/or encapsulating.

Figure 7:
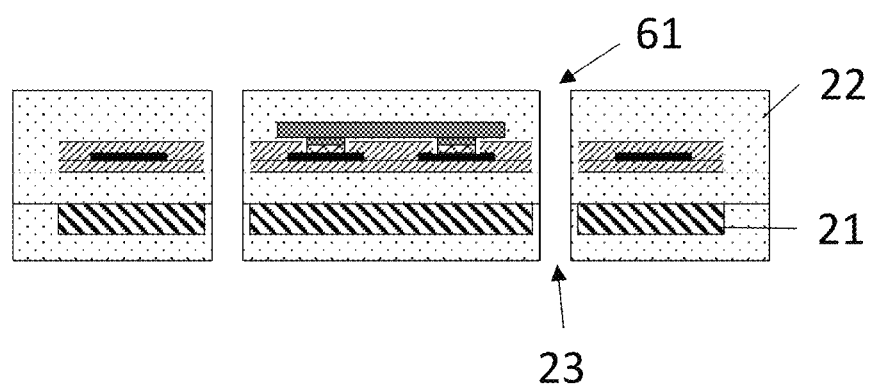
FIG. 7 shows an encapsulated stack of a deformable medical stent structure and a flexible electronic circuit, through which holes are provided, in accordance with embodiments of the present invention.

The method may comprise providing 108 regions of decreased thickness or (through)holes in the deformable electronic circuit. Referring to FIG. 7, the (through)holes may be provided in the deformable electronic circuit, or in the deformable electronic circuit and the two encapsulation layers 60,62, e.g. in alignment with openings in the deformable medical stent. For example, the holes may be provided in the circuit (and/or encapsulation) after attachment to the medical stent. It is an advantage of creating such holes after attachment to the medical stent that strain in the deformable electronic circuit may be reduced. The method may also comprise manufacturing 109 the deformable electronic circuit, e.g. before attachment to the stent.

FIG. 5 shows exemplary steps in a process for manufacturing 109 the deformable electronic circuit. Manufacturing 109 the deformable electronic circuit may comprise providing a first electrically insulating layer 52, e.g. a polyimide film. For example, the electrically insulating layer, e.g. the polyimide film, may have a thickness in the range of 1 μm to 20 μm, e.g. in the range of 2.5 μm to 10 μm, e.g. in the range of 5 μm to 6 μm, e.g. 5.5 μm. The electrically insulating layer may be fabricated, e.g. spin coated, on a suitable carrier substrate 51, such as a glass substrate. For example, a PI-2611 polyimide film may be spin-coated on a glass substrate.

Manufacturing 109 the deformable electronic circuit may comprise providing a metal layer 53 on, e.g. directly on, the electrically insulating layer 52. For example, the metal layer may have a thickness in the range of 0.5 μm to 2 μm, e.g. about 1 μm. The metal layer may be a copper layer, e.g. which may be advantageous in view of costs. The metal layer may be a gold and/or platinum layer, e.g. which may be advantageous in view of biocompatibility. For example, the metal 53, e.g. a thin film metallization, may be sputtered onto the electrically insulating layer 52.

Manufacturing 109 the deformable electronic circuit may further comprise patterning 54 the metal layer 53, e.g. to define conductive tracks in accordance with a predetermined electronic circuit design. This step may comprise processes as known in the art of (flexible) electronic circuit processing, such as photolithographic techniques and/or etching, e.g. wet etching.

Manufacturing 109 the deformable electronic circuit may comprise providing a second electrically insulating layer 55, e.g. a second polyimide film, on, e.g. directly on top of, the patterned metal layer 53. The second electrically insulating layer 55 may be provided by similar methods as described hereinabove for the first electrically insulating layer, and may have a similar thickness and/or composition.

Manufacturing 109 the deformable electronic circuit may comprise providing openings and/or vias 56 through the second electrically insulating layer 55, e.g. such as to locally provide access to the underlying metal layer 53, e.g. for electrical contacts and/or connections.

Manufacturing 109 the deformable electronic circuit may comprise patterning 57 the first and second electrically insulating layers, e.g. such as to locally remove the (e.g. all) material on the substrate 51. The step of patterning 57 may locally remove material on the substrate in locations corresponding to the regions of decreased thickness or (through) holes in the deformable electronic circuit, e.g. as discussed hereinabove.

For example, the first and second electrically insulating layers may be locally removed in parts of the deformable circuit, e.g. where the metal layer is absent and/or where no components are to be attached to the circuit, e.g. such that flexibility of the deformable electronic circuit is improved and/or such that mechanical strain is reduced or avoided, when attached to the medical stent, on returning the medical stent to its substantially cylindrical shape. For example, the first and second electrically insulation layers may be locally removed in locations that substantially correspond to openings in the medical stent (e.g. when properly aligned to the medical stent on attachment).

Manufacturing 109 the deformable electronic circuit may comprise operably attaching (e.g. mounting) at least one electronic component 58, such as a light emitting diode, a sensor element, a controller or microprocessor, etc., on the deformable electronic circuit, e.g. after providing the openings and/or vias 56 through the second electrically insulating layer 55 and/or after patterning 57 the first and second electrically insulating layers. For example, a conductive glue 59 may be applied, e.g. by stencil printing, on (e.g. on electrical connectors of) the at least one electronic component and/or on at least a part of the metal layer 53 that was exposed by the step of providing the openings and/or vias 56, and the at least one electronic component 58 may be joined by the conductive glue 59 to the deformable electronic circuit, e.g. to the exposed part of the metal layer 53.

Manufacturing 109 the deformable electronic circuit may comprise releasing the deformable electronic circuit from the substrate 51, e.g. after attaching the at least one electronic component 58, for example to transfer the deformable electronic circuit. Manufacturing 109 the deformable electronic circuit may comprise embedding the deformable electronic circuit, e.g. after being released from the substrate, in an insulating material 60, e.g. in a thermoplastic elastomer, such as thermoplastic polyurethane, e.g. such as to form the at least two insulating layers referred to hereinabove.

The method comprises (re)shaping 107 the deformed medical stent having the deformable electronic circuit attached thereon into the substantially cylindrical shape. For example, for a stent having elastic or super-elastic properties, the step of shaping 107 the deformed medical stent into the substantially cylindrical shape may comprise releasing the temporary fixation 103. For example, for a stent comprising an SMA material, the step of shaping 107 the deformed medical stent into the substantially cylindrical shape may comprise letting the hybrid structure, i.e. the stent having the deformable electronic circuit attached thereon, retrieve its parent shape, e.g. the substantially cylindrical form. For example, the step of deforming 102 the (SMA) medical stent may be performed at a first temperature in which the SMA material is (substantially) in its martensitic phase, and the step of shaping 107 may be performed at a higher temperature than that temperature to return the material to its austenite phase. Thus, a stent comprising an SMA material may advantageously allow a temporary deformation, e.g. to the planar shape, while this deformation can be (substantially) fully reversible, e.g. by retaining a shape memory of the parent shape, e.g. to the cylindrical shape.

For example, after performing a method in accordance with embodiments of the present invention, the stent having the deformable electronic circuit attached thereon may be inserted into a catheter 25, e.g. a micro-catheter, e.g. as illustrated in FIG. 2. This catheter may have a diameter that is smaller than the diameter of the substantially cylindrical shape. This can be advantageously performed due to the deformable properties of the stent and the deformable electronic circuit. Furthermore, the elastic or super-elastic properties of the stent may enable an efficient and effective expansion of the hybrid structure after deployment by the catheter, e.g. in the body. The hybrid structure may be deformed by elongation (e.g. relative to the substantially cylindrical shape) when pulled through the catheter.

In embodiments of the present invention in which the deformable electronic circuit is provided with regions of reduced thickness or holes, these regions or holes may advantageously improve the deformability of the circuit, and hence of the hybrid structure. Furthermore, when these regions or holes are aligned with openings in the medical stent, a hindering of the original mechanics of the medical stent due to the deformable electronic circuit attached thereto is advantageously reduced or avoided. For example, this may enable a stent comprising an SMA material to easily exert force on the deformable electronic circuit when restoring its substantially cylindrical shape.

A method in accordance with embodiments of the present invention may comprise determining a residual deformation of the medical stent having the deformable electronic circuit attached thereon in its substantially cylindrical shape relative to the substantially cylindrical shape of the medical stent, without the deformable circuit attached thereon. For example, a (small) elastic deformation compared to the design of the stent at rest can be determined. For example, this determining the residual deformation may comprise scanning the hybrid structure, e.g. by optically scanning. Additionally or alternatively, the structure of the medical stent having the deformable electronic circuit in its substantially planar shape may be determined. The method may comprise adjusting the design of (further) medical stents to account for a deviation from the cylindrical shape due to attachment of the deformable electronic circuit, e.g. by taking the determined residual deformation or the determined structure of the hybrid structure (e.g. a pilot item for future production) in its cylindrical and/or planar configuration into account, for example to reduce the residual deformation. The method may comprise adjusting the design of the deformable electronic circuit, e.g. by taking the determined residual deformation or the determined structure of the hybrid structure (e.g. a pilot item for future production) in its cylindrical and/or planar configuration into account, for example to reduce the residual deformation.

Referring to FIG. 1, an exemplary deformable medical stent A,B in accordance with embodiments of the present invention is shown.

Referring to FIG. 2, the deformable medical stent comprises a deformable medical stent structure 21 that is adapted for being deployed in a substantially cylindrical shape in the body, e.g. in a blood vessel. The deformable medical stent structure, i.e. the hybrid structure comprising the deformable medical stent and the deformable electronic circuit attached thereon, may be reversibly deformable between a substantially planar shape and a substantially cylindrical shape, e.g. by bending and/or rolling the stent in its substantially planar shape around an axis to obtain the substantially cylindrically symmetric shape. The deformable medical stent structure 21 may comprise a three-dimensional mesh. The deformable medical stent structure may be a deformable intravascular stent, e.g. a deformable stent that can be deployed inside a blood vessel. The deformable medical stent may be a flexible and more preferably a stretchable medical stent. The deformable medical stent structure may comprise a self-expanding intravascular stent.

In embodiments in accordance with the present invention, the deformable medical stent structure may comprise, e.g. may be composed of, an elastic material or a super-elastic material. The deformable medical stent may comprise, e.g. may be composed of, a shape-memory alloy (SMA). For example, the medical stent structure comprising the shape-memory alloy may have a stable geometrical configuration in its austenite phase. This stable geometrical configuration may correspond to the substantially cylindrical shape. For example, the shape memory alloy may comprise a Nickel-Titanium alloy, e.g. nitinol, or alloys comprising Nickel and Titanium, such a Nickel-Titanium-Hafnium or Nickel-Titanium-Palladium alloy. For example, the SMA material may comprise a Nickel-Titanium alloy having about 45% to 60 wt % of Nickel, e.g. a ratio of Ni/Ti in the range of 50:50 to 51.5:48.5. Other exemplary SMA materials include Silver-Cadmium, Gold-Cadmium, Copper-Aluminium-Nickel, Copper-Tin, Copper-Zinc, Iron-Platinum, Manganese-Copper, Iron-Manganese-Silicon, Copper-Nickel-Aluminium, Copper-Nickel-Gallium, Nickel-Iron-Gallium, Titanium-Niobium, and Nickel-Manganese-Gallium. The deformable medical stent structure may comprise a coating on the shape memory alloy material to provide or improve biocompatibility, such as a passive titanium oxide layer, e.g. $TiO_2$.

The deformable medical stent structure may comprise one or more wires or struts (e.g. of the SMA material) that are shaped, e.g. intertwined or joined, to form a three-dimensional mesh structure. Alternatively, such mesh structure may also be manufactured by perforating a hollow cylinder, e.g. by laser cutting. The mesh structure may form the cylindrical substantially cylindrical shape, e.g. in which the substantially cylindrical shape is interrupted by a longitudinal cut such that the mesh structure can be flattened into the substantially planar shape. For example, the mesh structure may comprise a wire (or wires) having a diameter in the order of 20 μm to 150 μm, e.g. in the range of 50 μm to 75 μm.

The deformable medical stent comprises a deformable electronic circuit 22 attached onto the deformable medical stent structure 21. The deformable electronic circuit may comprise an active electronic circuit, e.g. an integrated circuit comprising at least one active electronic component. The active electronic component may, for example, comprise a light emitting diode.

The deformable electronic circuit 22 may comprise at least one biostimulator element, such as at least one electrode for electrical stimulation and/or at least one light source for optical stimulation, e.g. light emitting diodes (LEDs). Alternatively, the deformable electronic circuit 22 may be electrically (e.g. operably) connected to such at least one biostimulator element comprised in the deformable medical stent, e.g. attached thereon separately from the deformable electronic circuit. Thus, a LED may be integrally formed on or in the deformable electronic circuit, or attached to the deformable electronic circuit, e.g. soldered, glued by conductive glue or attached by another suitable technique for operably connecting electronic components to a deformable integrated circuit. However, the LED or LEDs may also be attached to the medical stent structure separately and connected to the deformable electronic circuit, e.g. by (a) wire(s). For example, referring to FIG. 2 and FIG. 4, a LED 24 may be attached at a node 41 (e.g. a joint) of a mesh structure of the medical stent, e.g. by gluing, suturing or by another attachment technique known in the art, and connected to the deformable electronic circuit. For example, connecting wires may be wrapped around wires or struts of the mesh structure of the deformable medical stent structure, or interconnecting metal lines may be integrated in the deformable electronic circuit.

The at least one biostimulator element may comprise a blue light emitting LED having an output power in the range of 1 mW to 100 mW, e.g. in the range of 5 mW to 25 mW, e.g. 10 mW. For example, the deformable electronic circuit may comprise a pulse frequency generator for generating a predetermined frequency of stimulation pulses for the biostimulator element, e.g. to generate an optical stimulation in the range of 1 Hz to 200 Hz, e.g. in the range of 5 Hz to 50 Hz, e.g. 10 Hz.

The deformable electronic circuit may be attached to the deformed medical stent structure on a side thereof that is directed radially inward in the substantially cylindrical shape. For example, an exemplary medical stent A having the circuit attached thereto on this side is shown in FIG. 1. Alternatively or additionally, the deformable electronic circuit, or a further deformable electronic circuit, may be attached to the deformed medical stent structure on a side thereof that is directed radially outward in the substantially cylindrical shape. For example, an exemplary medical stent B having the circuit attached thereto on this side is shown in FIG. 1.

For example, a first deformable electronic circuit may be attached on a first side of the deformable medical stent structure and a second deformable electronic circuit may be attached on a second side of the deformable medical stent structure. The first deformable electronic circuit and the second deformable electronic circuit may be configured to operate independently, or may be interconnected. For example the first deformable electronic circuit may provide functionality directed towards the bloodstream when the stent is deployed in a structure of the body, e.g. in a blood vessel, for example for sensing of properties of the blood stream, and the second deformable electronic circuit may provide functionality directed towards the wall of, or tissue in the vicinity of, the structure in which the stent is deployed, e.g. of the blood vessel, such as electrical or optical stimulation, e.g. by LEDs or electrodes.

The deformable electronic circuit may comprise, for example, a patterned flexible printed circuit board (PCB). For example, the deformable electronic circuit may comprise a thin-film based flexible electronic circuit. For example, the deformable electronic circuit may comprise a polyimide substrate.

The deformable electronic circuit may comprise regions of decreased thickness or (through)holes 61, see FIG. 7. For example, the deformable electronic circuit may be perforated (e.g. etched away or laser-cut) in regions where no electronic circuit elements are provided in or on the deformable electronic circuit.

These regions of decreased thickness or holes 61 may correspond to openings 23 in the medical stent structure, e.g. may be aligned to such openings, e.g. as illustrated in FIG. 6. For example, the deformable medical stent structure may comprise a mesh structure, and the regions of reduced thickness or holes of the deformable electronic circuit may correspond to openings 23 in this mesh structure, e.g. to openings between a meshed wire (or wires, or joined struts) forming the deformable medical stent structure. Thus, the pattern of the regions or holes 61 in the deformable electronic circuit may overlap with the openings 23 in a mesh of the stent structure (even though the size of each region or hole is not necessarily identical to that of the corresponding opening in the stent structure). Electronic components on the deformable electronic circuit may thus be positioned at the positions of crosslinks and/or nodes and/or struts of the mesh forming the stent. For example, electrical conductors, e.g. signal and/or power supply lines for interconnecting electronic components of the circuit, may be aligned along the wires or struts of the mesh. For example, the deformable electronic circuit may be characterized by straight interconnection lines that may correspond to (at least part of) the mesh structure of the stent structure, when deformed to its substantially planar shape.

Referring to FIG. 7, the (through)holes in the deformable electronic circuit may be provided through the deformable electronic circuit, or through the deformable electronic circuit and the encapsulation material 60,62 discussed further hereinbelow, e.g. in alignment with openings in the deformable medical stent structure.

However, in other embodiments in accordance with embodiments of the present invention, the regions or holes in the deformable electronic circuit may not necessarily overlap or fully overlap with the openings in the medical stent structure. For example, the deformable electronic circuit may comprise meandering electrical conductors, e.g. signal and/or power supply lines, such that these electrical conductors can be less prone to damage due to stretching, e.g. elongation in at least one direction, of the deformable circuit. For example, the meandering electrical conductors may (or may not) be partly aligned with struts of the medical stent structure, but may also cover at least in part openings in the medical stent structure. It is an advantage that the deformable electronic circuit may be stretched and/or compressed (e.g. when the deformable medical stent is deformed on deployment in the body) without damaging the electrical conductors, while also providing more freedom in routing by not limiting the available space for the electrical conductors to those areas of the circuit that do not correspond with openings in the medical stent structure.

Referring to FIG. 5, the deformable electronic circuit may comprise an electrically insulating material 60, e.g. at least two insulating layers, e.g. a bottom layer and a top layer, for electrically isolating the deformable electronic circuit from the medical stent structure. For example, the electronic circuit, e.g. electronic components and/or electrical conductors thereof, may be embedded in the electrically insulating material 60, e.g. between two insulating layers. The insulating material may comprise an electrically insulating polymer material, e.g. a thermoplastic elastomer and/or a thermoset flexible polymer and/or a hyperelastic polymer. The insulating material may comprise a material such as polyimide, thermoplastic polyurethane (TPU) or other polymer insulators suitable for flexible electronic circuits known in the art. For example, polyimide may be sufficiently flexible at thicknesses in the range of 10 to 100 μm, e.g. in the range of 25 μm to 50 μm. Preferably, the at least two insulating layers may have bidirectional barrier layer properties, e.g. such as to protect the electronic circuit from the environment in the body, e.g. molecules in the body that could cause malfunction by corrosion of the electronic circuit, and such as to block any diffusion of non-biocompatible materials in the deformable electronic circuit into the body. Methods known in the art for making electronics biocompatible may be applied in providing the deformable electronic circuit.

Advantageously, the deformable electronic circuit may be multi-layered, e.g. to provide complex electronic functionality. For example, the deformable electronic circuit may comprise a wireless data transmitter and/or receiver. Likewise, the deformable electronic circuit may comprise a wireless power receiver for wirelessly receiving a power supply from an external source. However, embodiments of the present invention are not necessarily limited thereto, e.g. the deformable electronic circuit may be configured to perform a predetermined function autonomously, e.g. without requiring data exchange with the outside world, or the deformable electronic circuit may comprise at least one wire lead, e.g. a conductive wire, such as an electrically insulated electrical wire, to exchange data and/or to receive power from the outside world.

The deformable electronic circuit may be attached to the deformed medical stent structure by a durable mechanical connection, e.g. by glue, over the entire contact surface between the stent structure and the circuit, but such durable mechanical connection may alternatively also be provided only between a plurality of (discrete) contact points between the deformable electronic circuit and the deformable medical stent structure.

The medical stent may comprise an encapsulation material encapsulating the deformable electronic circuit and the deformed medical stent structure, e.g. between two encapsulation layers, e.g. such that the deformable electronic circuit together with the medical stent structure are sandwiched between two layers that are fused and/or glued together. At least part of the encapsulation material, e.g. a bottom or top layer thereof, may be formed by the electrically insulating material 60 discussed hereinabove.

Referring to FIG. 6, the medical stent may comprise a bottom encapsulation layer 62, on which the deformable electronic circuit and the deformable medical stent structure are provided, and a top encapsulation layer 60 provided on top of the deformable electronic circuit and the deformable medical stent structure. The bottom encapsulation layer and the top encapsulation layer may be glued or fused together to encapsulate the deformed medical stent structure and the deformable electronic circuit. For example, the encapsulation material, e.g. the bottom and top encapsulation layers, may comprise a polymer material, such as polyimide, thermoplastic polyurethane (TPU) or other suitable materials.

Referring to FIG. 5, the deformable electronic circuit may comprise a first electrically insulating layer 52, e.g. a polyimide film, such as a PI-2611 polyimide film, and a metal layer 53 provided thereon, e.g. directly thereon on. For example, the electrically insulating layer, e.g. the polyimide film, may have a thickness in the range of 1 μm to 20 μm, e.g. in the range of 2.5 μm to 10 μm, e.g. in the range of 5 μm to 6 μm, e.g. 5.5 μm. The metal layer may have a thickness in the range of 0.5 μm to 2 μm, e.g. about 1 μm. The metal layer may be a copper and/or gold and/or platinum layer. The metal layer 53 may be patterned 54, e.g. to define conductive tracks in accordance with a predetermined electronic circuit design.

The deformable electronic circuit may comprise a second electrically insulating layer 55, e.g. a second polyimide film, on, e.g. directly on top of, the patterned metal layer 53. The second electrically insulating layer 55 may have a similar thickness and/or composition as the first electrically insulating layer.

The deformable electronic circuit may comprise openings and/or vias 56 through the second electrically insulating layer 55, e.g. such as to locally provide access to the underlying metal layer 53, e.g. for electrical contacts and/or connections.

The first and second electrically insulating layers may be patterned 57, e.g. such as to locally remove the (e.g. all) material of the aforementioned layers in locations corresponding to the regions of decreased thickness or (through) holes in the deformable electronic circuit, e.g. as discussed hereinabove.

The deformable electronic circuit may comprise at least one electronic component 58 operably attached (e.g. mounted) onto the metal layer at the openings and/or vias 56. The at least one electronic component may comprise a light emitting diode, a sensor element, a controller and/or microprocessor, etc.

The deformable electronic circuit may comprise a conductive glue 59 in between the at least one electronic component and at least a part of the metal layer 53 that was exposed by the openings and/or vias 56.

The invention claimed is:

1. A method for integrating an electronic circuit in or on a medical stent, the method comprising:
    obtaining a deformable medical stent in a substantially planar shape, wherein said deformable medical stent is adapted for being deployed in a substantially cylindrical shape in the human or animal body;
    attaching a deformable electronic circuit onto the deformable medical stent when in said substantially planar shape thereby forming a deformable hybrid structure, wherein the deformable circuit comprises regions of decreased thickness and/or holes, and wherein said attaching of said deformable electronic circuit comprises aligning said regions or holes to openings in said mesh structure of said deformable medical stent and/or wherein said providing said regions and/or holes in said deformable electronic circuit is performed after said attaching; and
    shaping said deformable hybrid structure into said substantially cylindrical shape,
    wherein the deformable stent comprises at least one wire and/or a plurality of struts, configured to form a three-dimensional mesh structure, wherein said three-dimensional mesh structure forms said substantially cylindrical shape and wherein said substantially cylindrical shape is interrupted by a longitudinal cut such that said mesh structure can be flattened into said substantially planar shape.

2. The method of claim 1, wherein said obtaining a deformable medical stent in a substantially planar shape comprises the step of obtaining a deformable medical stent in a substantially cylindrical shape and deforming said substantially cylindrical shape into said substantially planar shape.

3. The method of claim 1, wherein said deformable electronic circuit is a stretchable electronic circuit.

4. The method of claim 1, wherein said deformable hybrid structure is a reversibly deformable hybrid structure.

5. The method of claim 1, wherein attaching of said deformable electronic circuit comprises obtaining said deformable electronic circuit comprising at least one active electronic component.

6. The method of claim 1, wherein said deformable electronic circuit comprises at least one light emitting diode and/or at least one sensor element, and deformable electrical connections connected to said at least one light emitting diode and/or said at least one sensor element.

7. The method of claim 1, wherein said obtaining of said deformable medical stent comprises obtaining said deformable medical stent comprising or consisting of an elastic material or a super-elastic material.

8. The method of claim 1, wherein said obtaining of said deformable medical stent comprises obtaining said deformable medical stent comprising or consisting of a shape-memory alloy, having a stable geometrical configuration in its austenite phase that corresponds to said substantially cylindrical shape.

9. The method of claim 8, wherein said obtaining said deformable medical stent comprises deforming said deformable medical stent into said substantially planar shape at an ambient temperature below room temperature to bring said SMA material in its martensitic phase.

10. The method of claim 1, comprising temporarily fixating (103) said deformable medical stent in said substantially planar shape.

11. The method of claim 1, wherein said attaching of said deformable electronic circuit comprises attaching said deformable electronic circuit onto said deformable medical stent on a side thereof that is directed radially inward in the substantially cylindrical shape and/or attaching said deformable electronic circuit, or a further deformable electronic circuit, on a side thereof that is directed radially outward in the substantially cylindrical shape.

12. The method of claim 1, wherein said attaching of said deformable electronic circuit to said deformed medical stent comprises encapsulating the deformable electronic circuit and the deformed medical stent in between two encapsulation layers that are fused and/or glued together.

13. The method of claim 1, comprising manufacturing said deformable electronic circuit before said step of attaching.

* * * * *